United States Patent [19]

Bezman

[11] 4,428,753

[45] * Jan. 31, 1984

[54] CONTINUOUS EXTRACTIVE BLENDING PROCESS

[75] Inventor: Susan A. Bezman, Point Richmond, Calif.

[73] Assignee: Chevron Research Company, San Francisco, Calif.

[*] Notice: The portion of the term of this patent subsequent to Aug. 16, 2000 has been disclaimed.

[21] Appl. No.: 277,440

[22] Filed: Jun. 25, 1981

[51] Int. Cl.³ .............................................. C10L 1/18
[52] U.S. Cl. ....................................... 44/56; 210/474
[58] Field of Search ............................ 44/56; 210/474

[56] References Cited

U.S. PATENT DOCUMENTS

| | | | |
|---|---|---|---|
| 2,288,532 | 6/1942 | Knapp | 210/474 |
| 2,591,672 | 4/1952 | Callerall | 44/56 |
| 2,756,607 | 5/1956 | Hess | 210/169 |
| 3,455,664 | 7/1969 | Rosscup et al. | 44/56 |
| 3,793,379 | 2/1974 | Rosscup et al. | 260/641 |
| 4,251,231 | 2/1951 | Baird | 44/56 |

*Primary Examiner*—J. V. Howard
*Attorney, Agent, or Firm*—D. A. Newell; S. R. La Paglia; S. H. Roth

[57] ABSTRACT

A continuous process for blending isopropanol from an aqueous solution of isopropanol directly into a stream of gasoline blending hydrocarbon by mixing the aqueous solution and the gasoline, rapidly separating the resulting mixture into two phases, for example, by passing it through water coalescer means and recovering the organic phase which consists essentially of the gasoline and isopropanol.

7 Claims, No Drawings

CONTINUOUS EXTRACTIVE BLENDING PROCESS

BACKGROUND OF THE INVENTION

The present invention relates to the production of oxygenated fuels. Specifically, the invention relates to a process for the production of an oxygenated fuel composition comprising isopropanol and gasoline in which isopropanol from an aqueous solution is simultaneously extracted from solution and blended with a gasoline blending hydrocarbon component.

There is a great need to produce high octane gasoline. However, the use of the traditional lead-containing gasoline additives has been largely discontinued. Moreover, refineries have experienced a shortage of isoparaffins, particularly isobutane which are generally reacted with excess olefins to produce alkylate, a high octane gasoline additive.

Oxygenated compounds such as ethanol, isopropanol and methyl-t-butyl ether are high octane components that are now finding their way into the motor gasoline pool. In making alcohols by the hydration of olefins, the raw product from the reactor generally contains a substantial quantity of water in addition to the alcohol. Dehydrating the aqueous alcoholic solution has heretofore required energy intensive procedures, such as extractive distillation or azeotropic distillation.

The present invention provides an economical method for dehydrating an aqueous alcoholic solution of isopropanol which does not require any of the energy intensive extraction or distillation procedures.

SUMMARY OF THE INVENTION

The present invention provides a continuous process for blending isopropanol from an aqueous solution of isopropanol into a stream of gasoline blending hydrocarbons. The process comprises mixing an aqueous solution of isopropanol having an isopropanol content of at least about 50% with a gasoline blending hydrocarbon stream, allowing the mixture to separate into two phases, an organic phase which consists essentially of the gasoline blending hydrocarbon and the isopropanol and an aqueous phase which consists essentially of water, and then recovering the organic phase. In an embodiment of the continuous process of the invention, the mixing is accomplished by use of in-line mixers and the phase separation is accomplished rapidly, for example, by using water coalescer means.

DESCRIPTION OF THE PREFERRED EMBODIMENTS

The present process is preferably used in conjunction with a process for producing isopropanol by the direct hydration of propylene such as is disclosed in my U.S. patent application entitled "Propylene Hydration," filed concurrently herewith and incorporated by reference herein. In that process the crude liquid product from the hydration reactor contains water, isopropanol, diisopropyl ether and perhaps some trace amounts of $C_4$ olefin-derived ethers and/or alcohols. After caustic neutralization, the by-product diisopropyl ether is removed by simple distillation in a first distillation column. The bottoms from the first distillation column containing primarily water and isopropanol are then distilled again to produce the isopropanol-water azeotrope which is composed of 87.8 weight percent isopropanol and 12.2 weight percent of water.

The process of the present invention is concerned with the treatment of such an aqueous isopropanol solution and allows one to blend isopropanol from the azeotrope, or any aqueous isopropanol solution having an isopropanol content of at least about 50% directly into a gasoline blending hydrocarbon, thus eliminating the need for azeotropic distillation. The process of the present invention also eliminates any requirement for extractors such as mechanically agitated columns, rotary-agitated columns, reciprocating plate columns and centrifugal extractors, the operation of which consume much energy, decreasing the efficiency of a process in which isopropanol can be incorporated into the motor gasoline pool from an aqueous solution.

In a process according to the invention, an aqueous isopropanol solution is mixed with gasoline blending hydrocarbons. The gasoline blending hydrocarbon may be any hydrocarbon that can be added to the motor gasoline pool including straight run, alkylate, FCC gasoline, reformate or their mixtures such as Chevron Unleaded Regular gasoline (ULR). The gasoline blending hydrocarbons may also comprise diesel and/or jet fuel. The gasoline blending hydrocarbons extract the isopropanol out of the aqueous solution, and after the phase separate, an organic phase which comprises an oxygenated fuel composition is produced. In the process of the invention, isopropanol is continuously, simultaneously extracted from an aqueous solution and blended with a component of the motor gasoline pool.

In a batch process which is the subject of my U.S. patent application entitled "Extractive Blending Process," filed concurrently herewith and incorporated by reference herein, gasoline blending hydrocarbons are mixed with an isopropanol-water azeotrope and the mixture is allowed to separate into two phases, for example, in a large settling tank. The organic phase consists essentially of the gasoline blending hydrocarbons and the isopropanol. The aqueous phase consists essentially of water.

Separation of the mixture into two phases can take a long time but in accordance with the process of the present invention, the phase separation is achieved rapidly without any detrimental effect on the composition of the organic phase. The present invention, therefore, provides a continuous process for producing an oxygenated fuel composition from an aqueous solution of isopropanol.

In accordance with this process, an aqueous solution of isopropanol, preferably the azeotrope, is mixed with a stream of gasoline blending hydrocarbons by using a conventional in-line mixer such as those manufactured by Komax Systems, Inc. A milky emulsion forms on mixing. Surprisingly, this emulsion separates rapidly into two phases by passing it through a water filter coalescer such as a Racor Model 2000 SM Filter Separator, preferably after modification to avoid deterioration of polymeric components. Other such separators are available from Facet Enterprises, Inc. Although separation is rapid, extraction is essentially complete. The composition of the resulting phases is unaffected despite the short phase separation time.

The water in the emulsion may be coalesced by employing any conventional water coalescer means including coalescers, separating membranes and certain electrical devices.

Coalescers are generally mats, beds or layers of porous or fibrous solids whose properties are especially suited for the purpose at hand. Their action appears to be twofold: (1) protective, high-viscosity films surrounding the dispersed-phase droplets are ruptured and wiped away by the coalescer; (2) the droplets preferentially wet the solid, attach themselves thereto, and grow in size by coalescing with others similarly caught. The enlarged drops are then carried away by the flowing stream of continuous phase. The coalescer is, therefore, generally a solid of large surface to volume ratio, with uniformly small passages to ensure action on all the dispersion, of low pressure drop for flow, and for best results it should be preferentially wet by the dispersed phase.

A coalescer should also be mechanically strong enough to resist the pressure drop prevailing, and chemically inert toward the liquids. Beds of granular solids such as sand and diatomaceous earth, and bats of excelsior, steel wool, copper turnings, glass wool, Fiberglas, and the like have been used. Materials such as mineral wool may be coated with substances such as silicones and resids to provide the preferential wetting characteristics.

Water coalescers and method for resolving water and oil emulsions are disclosed in U.S. Pat. Nos. 2,288,532; 2,522,378 and 2,746,607 which are incorporated by reference herein.

If the capillary size of a porous substance is very small, then the liquid which preferentially wets the solid may flow through the capillaries readily, but strong interfacial films block the capillaries for flow of non-wetting liquid. Sufficient pressure will cause disruption of the films and permit passage of the non-wetting liquid, but regulation of the pressure commensurate with the pore size permits perfect phase separation. Separating membranes of this type are generally made of a variety of materials such as porcelain, resin-coated paper, and the like, and may be either hydrophilic or hydrophobic in character. They are generally made thin to permit maximum passage of the wetting liquid. In practice, the dispersion is usually first passed through a coalescer to relieve the load on the membrane.

Subjecting electrically conducting emulsions or dispersions to high-voltage electric fields may cause rupture of the protective film about a droplet and thus induce coalescence. This has been used particularly for the desalting of petroleum emulsified with brine, and for similar applications. See, e.g., U.S. Pat. No. 2,527,690 incorporated by reference herein.

By using this continuous scheme, it is possible to obtain substantial capital savings. After appropriate scale-up, the estimated capital investment for extractive blending in a plant producing two thousand barrels per day of isopropanol (about twenty thousand barrels per day of a 10% isopropanol-gasoline blend) would be only about forty thousand dollars for the requisite pumps and large scale water coalescer instead of the high costs associated with energy-intensive distillation purifications.

In this continuous process, the aqueous isopropanol solution should preferably contain at least about 50 weight percent isopropanol. The isopropanol-water azeotrope is particularly preferred. For each volume of azeotrope, at least 2 volumes, preferably about 10 volumes of hydrocarbon extractant should be used. For more concentrated aqueous solutions, less hydrocarbon is required for extractive blending.

EXAMPLES

The following Examples are set forth in Table I to demonstrate the process of the present invention and its advantages. The Examples are merely illustrative and are not intended to be construed as a limitation.

In the runs set forth in Table I, the separations were accomplished by gravity in a separatory funnel, except for those marked with an asterisk for which a Racor Model 2000 SM Filter Separator was used.

TABLE I

| Run | Extraction Mixture | Weight (g) | Volume (cc) | Organic Phase Wt % Extractant/ Alcohol/Water | Aqueous Phase Wt % Extractant/ Alcohol/Water | % Alcohol Extracted | % Water Removed |
|---|---|---|---|---|---|---|---|
| A | LSR/IPA-H$_2$O(A) | NA/NA/NA | 1000/100 | 90.2/9.4/0.40 | 0/28.5/71.5 | 96. | 68. |
| B | ULR/IPA-H$_2$O(A) | 744.9/79.59 | 1000/100 | 91.2/8.3/0.41 | 0/25/75 | 97. | 65. |
| C | ULR/IPA-H$_2$O(A) | 374.8/80.66 | 500/100 | 83.5/15.3/1.2 | 0/31.3/68.7 | 97. | 48. |
| D | ULR/IPA-H$_2$O(A) | 187.9/80.85 | 250/100 | 70.4/26.3/3.3 | 0/42/58 | 99. | 11. |
| *E | ULR/IPA-H$_2$O(A) | NA/NA | 250/100 | 70.4/26.3/3.3 | NA/NA/NA | NA | NA |
| F | ULR/EtOH-H$_2$O (90-10) | 372/40.3 | 500/50 | 92.6/7.0/0.44 | 6.3/73.4/20.4 | 77.3 | 56.5 |
| *G | ULR/EtOH-H$_2$O (90-10) | NA/NA | 500/50 | 92.8/6.8/6.4 | NA/NA/NA | NA | NA |
| *H | ULR/IPA-H$_2$O(A) | NA/NA | 1000/100 | NA/NA/.31 | NA/NA/NA | NA | NA |
| I | ULR/IPA-H$_2$O (75-25) | 368.5/41.85 | 500/50 | 92.2/7.5/0.35 | 0/22.3/77.7 | 94.8 | 86.9 |
| J | ULR/IPA-H$_2$O (75-25) | 554.5/42.06 | 750/50 | 94.8/5.01/0.22 | 0/20.8/79.2 | 92.8 | 82.8 |

NA = Not Analyzed

Runs A-E, and H-J of Table I include the results of conducting a process in accordance with the present invention and demonstrate the effects of the composition of the hydrocarbon extractant, the ratio of extractant to alcohol solution, and coalescer treatment. Runs A-D, I and J were gravity separations in which the parenthetically indicated amounts in weight percent of the extraction mixture components were mixed in a separatory funnel and the phases were allowed to separate. Runs E and H were filter coalescer treatments in accordance with the invention in which the extraction mixture components were mixed and passed through a Racor Model 2000 SM Filter Separator.

In Run A, a light straight run gasoline (LSR) was used as the extractant in a 10 to 1 volume ratio with the isopropanol-water azeotrope (IPA—H$_2$O(A)). The top layer after extraction consisted of 91.6% LSR, 8.1% IPA and 0.30% H$_2$O by volume. Over 96% of the isopropanol in the azeotrope was extracted in the gasoline.

About 68% of the water originally present is the azeotrope separated into a lower layer. In a commercial operation, the very small layer (<1/100 of the total gasoline volume) could be recycled to the azeotrope-producing distillation unit resulting in no net loss of isopropanol. The hydrocarbon layer (upper IPA-gasoline layer) had octane values about 4.3 F-1 and 2.9 F-2 units higher than the base gasoline used in the blending process. So gasoline upgrading is easily and economically accomplished by the process of the present invention.

Comparison of Runs A and B indicates that the nature of the hydrocarbon mixture does not significantly affect the composition or the relative quantities of the layers obtained.

Comparison of Run B and H and D with E demonstrates that rapid filter coalescer phase separation procedure and slow gravity phase separation procedure produce layers having the same relative composition and amount.

Runs B, C and D all using Chevron Unleaded Regular (ULR) demonstrate the effect of varying the hydrocarbon to azeotrope ratio. Initially, it is noted that for all ratios, no detectable amount of hydrocarbon is lost to the aqueous layer. In addition, more than 97% of the isopropanol was extracted into the hydrocarbon. As noted above, the isopropanol remaining in the aqueous phase could be recycled to the azeotrope-producing distillation unit to eliminate loss of isopropanol.

As the hydrocarbon to azeotrope ratio decreases, the amount of water in the resulting blend increases. At a ratio of 2.5 to 1 (Run D), the gasoline-isopropanol blend contains 3.3 weight percent water, an unacceptably high level. In such cases the relative amount of water can be reduced by simply adding more hydrocarbon blending components to the extracted mixture. This will also decrease the relative amount of isopropanol in the blend, which may be undesirable. A method which permits one to use lower hydrocarbon to azeotrope ratios and produce an oxygenated fuel composition having a lower residual water content is disclosed in my U.S. patent application entitled "Improved Extractive Blending Process," filed concurrently herewith and incorporated by reference herein.

Runs F and G demonstrate the unexpectedly beneficial results obtainable with the present process. For comparison in Run R, unleaded regular gasoline was used to extract ethanol out of a 90-10 wt. % ethanol-water mixture, which approximates the composition of the isopropanol-water azeotrope. At a hydrocarbon to aqueous solution ratio of 10:1, only 77.3% of the ethanol was extracted from the solution. Moreover, the aqueous phase contained 6.3% gasoline, whereas no gasoline was lost to this phase where isopropanol was used.

Ethanol may be extractively blended into gasoline from such mixtures of ethanol and water by the method described in my U.S. application entitled "Improved Extractive Blending Process."

If, in the case of isopropanol, too much water remains in the hydrocarbon layer, it may be removed by treating it in accordance with the method disclosed in my U.S. patent application entitled "Oxygenated Fuel Dehydration," filed concurrently herewith and incorporated by reference herein.

It is seen, therefore, that by employing the process of the present invention, all distillations except a preliminary distillation to produce, for example, the isopropanol-water azeotrope are eliminated and replaced by the extractive blending of isopropanol directly into gasoline.

Although the present invention has been described with reference to specific examples and embodiments, it is clear that many modifications are possible without departing from the scope of the invention which is defined by the appended claims.

What is claimed is:

1. A continuous process for blending isopropanol from an aqueous solution into a gasoline blending hydrocarbon stream comprising:
    (a) mixing at atmospheric pressure and ambient temperature a first stream consisting essentially of an aqueous isopropanol solution having an isopropanol content of at least about 50% with a second stream consisting essentially of a gasoline blending hydrocarbon stream;
    (b) passing the resulting mixture through water coalescer means to rapidly separate the mixture into two phases; and
    (c) recovering an organic phase which consists essentially of isopropanol and the gasoline blending hydrocarbon stream.

2. The process of claim 1, wherein the aqueous isopropanol solution is the isopropanol-water azeotrope.

3. The process of claim 1, wherein the gasoline blending hydrocarbon stream is a mixture of hydrocarbons boiling in the gasoline range.

4. The process of claim 1, wherein the gasoline blending hydrocarbon stream and the isopropanol solution are mixed at a volume ratio of at least about 2:1.

5. The process of claim 2, wherein the gasoline blending hydrocarbon stream and the isopropanol-water azeotrope are mixed at a volume ratio of from about 2:1 to 15:1.

6. The process of claim 5 wherein the volume ratio is about 10:1.

7. The process of claim 1, wherein the water coalescer means is a filter separator.

* * * * *

UNITED STATES PATENT AND TRADEMARK OFFICE
CERTIFICATE OF CORRECTION

PATENT NO. : 4,428,753
DATED : January 31, 1984
INVENTOR(S) : Susan A. Bezman

It is certified that error appears in the above-identified patent and that said Letters Patent are hereby corrected as shown below:

Col. 2, line 28, "phase" (1st occurr.) should read --phases--.

Col. 2, line 52, "mixed with a stream" should read --mixed at atmospheric pressure and ambient temperature--.

Signed and Sealed this

Nineteenth Day of February 1985

[SEAL]

Attest:

DONALD J. QUIGG

Attesting Officer     Acting Commissioner of Patents and Trademarks